United States Patent
Bherwani et al.

(10) Patent No.: US 11,497,457 B2
(45) Date of Patent: Nov. 15, 2022

(54) GADOLINIUM DEPOSITION DETECTION AND QUANTIFICATION

(71) Applicant: GE Healthcare AS, Oslo (NO)

(72) Inventors: Anand Bherwani, Waukesha, WI (US); Bob Senzig, Waukesha, WI (US); Scott D. Slavic, Waukesha, WI (US)

(73) Assignee: GE HEALTHCARE AS, Oslo (NO)

( * ) Notice: Subject to any disclaimer, the term of this patent is extended or adjusted under 35 U.S.C. 154(b) by 0 days.

(21) Appl. No.: 17/050,492

(22) PCT Filed: Apr. 25, 2019

(86) PCT No.: PCT/EP2019/060689
§ 371 (c)(1),
(2) Date: Oct. 26, 2020

(87) PCT Pub. No.: WO2019/207078
PCT Pub. Date: Oct. 31, 2019

(65) Prior Publication Data
US 2021/0186447 A1   Jun. 24, 2021

Related U.S. Application Data

(60) Provisional application No. 62/662,373, filed on Apr. 25, 2018.

(51) Int. Cl.
*A61B 6/00* (2006.01)
*A61B 6/03* (2006.01)

(52) U.S. Cl.
CPC .............. *A61B 6/481* (2013.01); *A61B 6/032* (2013.01); *A61B 6/4241* (2013.01); *A61B 6/482* (2013.01); *A61B 6/505* (2013.01)

(58) Field of Classification Search
CPC ....... A61B 6/481; A61B 6/032; A61B 6/4241; A61B 6/482; A61B 6/505; G06T 2211/408; G06T 2211/416; G06T 11/006; A61K 31/28
See application file for complete search history.

(56) References Cited

U.S. PATENT DOCUMENTS

| | | | |
|---|---|---|---|
| 2008/0310582 A1 | 12/2008 | Flohr et al. | |
| 2012/0076258 A1 | 3/2012 | Chandra et al. | |
| 2012/0076377 A1 | 3/2012 | Dutta et al. | |
| 2013/0308847 A1* | 11/2013 | Schirra | G06T 11/005 382/131 |
| 2017/0095578 A1 | 4/2017 | Karam et al. | |

OTHER PUBLICATIONS

International Search Report received in Application No. PCT/EP2019/060689, dated Jun. 26, 2019, 13 pages.
McDonald, et al., "Gadolinium Deposition in Human Brain Tissues after Contrast-enhanced MR Imaging in Adult Patients without Intracranial Abnormalities," Original Research, Neuroradiology, vol. 285, No. 2, Nov. 2017, 9 pages.
Pan, et al., "Computed Tomography in Color: NanoK-Enhanced Spectral CT Molecular Imaging," NIH Public Access, Angew Chem Int. Ed Engl Dec. 10, 2010, 11 pages.
Aigbirhio, et al., "Efficient regioselective labelling of the CFC alternative 1,1,1,2-tetrafluoroethane (HFC-134a) with fuorine-18," ScienceDirect, Journal of Fluorine Chemistry, vol. 70, Issue 2, Feb. 1995, 3 pages.
Delesalle, et al., "Spectral Optimization of Chest CT Angiography with Reduced Iodine Load: Experience in 80 Patients Evaluated with Dual-Source, Dual-Energy CT," Original Research, Thoracic Imaging, Radiology: vol. 267: Number 1, Apr. 2013, 11 pages.
Lv, et al., "Differentiation of Small Hepatic Hemangioma from Small Hepatocellular Carcinoma: Recently Introduced Spectral CT Method," Original Research, Gastrointestinal Imaging, Radiology: vol. 259, No. 3, Jun. 2011, 10 pages.
Radia Diagnostic, 2022, Radiological Imaging Technology, Inc., Med. Phys. 38, (3), Mar. 2011, 12 pages.

\* cited by examiner

*Primary Examiner* — Courtney D Thomas
(74) *Attorney, Agent, or Firm* — Culhane Meadows, PLLC; Jeff B. Vockrodt

(57) ABSTRACT

The present invention relates to a method for the evaluation of tissue gadolinium deposition that offers advantages compared with known methods. Comparison of different gadolinium-based contrast agents (GBCAs) based on retention, organ distribution, washout and safety is facilitated using the methods of the present invention.

16 Claims, No Drawings

GADOLINIUM DEPOSITION DETECTION AND QUANTIFICATION

TECHNICAL FIELD OF THE INVENTION

The present invention relates to measurement of metal deposition in the tissue of a subject and in particular to where that metal is gadolinium.

DESCRIPTION OF RELATED ART

Current methods to detect and quantify retention of gadolinium (Gd) in the tissue of a patient require taking a tissue sample. A method for the non-invasive in vivo detection and quantification of Gd retention would be of value.

SUMMARY OF THE INVENTION

The present invention provides a method for antemortem detection and quantification of gadolinium retention in the tissue of a subject comprising imaging said subject using spectral computed tomography (CT) to obtain an image wherein gadolinium retention is detected and quantified based on its energy-dependent attenuation profile.

The present invention is advantageous compared with known methods. Determination of gadolinium deposition can be carried out on a living subject without the need to take a tissue sample from the subject. The present invention facilitates the assessment of different gadolinium-based contrast agents (GBCAs) for retention, organ distribution, washout and safety. Such an assessment is particularly facilitated by the present invention as greater sample sizes are permitted.

DETAILED DESCRIPTION OF THE PREFERRED EMBODIMENTS

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "tissue" takes its ordinary meaning in the field of biology, which is to say part of the body of a living thing that is made of similar cells, e.g. cardiac tissue of the heart.

The "subject" of the invention can be any human or animal subject. In one embodiment the subject of the invention is a mammal. In one embodiment said subject is an intact mammalian body in vivo. In another embodiment, the subject of the invention is a human. In one embodiment the subject of the invention is a subject to whom a gadolinium-based contrast agent has been previously administered.

The term "gadolinium-based contrast agent" defines in vivo contrast media consisting of molecules wherein chemical bonds are made between a gadolinium ion and a carrier molecule known as a chelating agent. The chelating agent serves to prevent release of gadolinium while maintaining its contrast properties. Different brands of gadolinium contrast medium use different chelating molecules. The contrast medium is injected intravenously into a subject as part of a magnetic resonance imaging (MRI) scan.

The term "computed tomography" (also "computed axial tomography" or "computer-aided tomography") refers to a medical imaging technique that makes use of computer-processed combinations of the data obtained from many X-ray measurements taken from different angles to produce cross-sectional (tomographic) images (or virtual "slices") of specific areas of a scanned subject, allowing a user to see inside the subject without cutting. The visual representations of the interior of a subject obtained can be used for clinical analysis, medical intervention, or to obtain a visual representation of the function of selected organs or tissues.

CT methodology is well known to those of skill in the art (as described for example in "Computed Tomography: Fundamentals, System Technology, Image Quality, Applications", $3^{rd}$ Edition 2011; Publicis Publishing: Willi A. Kalender, Ed.). In typical CT imaging systems, an x-ray source emits a fan-shaped beam towards a subject. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about a gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy discriminating (ED), multi energy (ME), and/or dual energy (DE) CT imaging system that may be referred to as an EDCT, MECT, and/or DE-CT imaging system. Such systems may use a scintillator or a direct conversion detector material in lieu of the scintillator. The EDCT, MECT, and/or DE-CT imaging system in an example is configured to be responsive to different x-ray spectra. For example, a conventional third generation CT system may acquire projections sequentially at different peak kilovoltage (kVp) levels, which changes the peak and spectrum of energy of the incident photons comprising the emitted x-ray beams. Energy sensitive detectors may be used such that each x-ray photon reaching the detector is recorded with its photon energy.

Techniques to obtain the measurements comprise: (1) scan with two distinctive energy spectra, and (2) detect photon energy according to energy deposition in the detector. EDCT/MECT/DE-CT provides energy discrimination and material characterization. For example, in the absence of object scatter, the system derives the behaviour at a different energy based on the signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials.

A principle objective of dual energy scanning is to obtain diagnostic CT images that enhance contrast separation within the image by utilizing two scans at different chromatic energy states. A number of techniques have been proposed to achieve dual energy scanning including acquiring two scans either (1) back-to-back sequentially in time where the scans require two rotations around the subject, or (2) interleaved as a function of the rotation angle requiring one rotation around the subject, in which the tube operates at, for instance, 80 kVp and 140 kVp potentials. High frequency generators have made it possible to switch the kVp potential of the high frequency electromagnetic energy projection source on alternating views. As a result, data for two dual energy images may be obtained in a temporally interleaved fashion rather than two separate scans made several seconds apart as required with previous CT technology.

Dual kVp CT scanning may be performed by, for instance, scanning first at one kVp and then at a second kVp. To overcome a possible mis-registration of the images acquired at the two kVps, kVp modulation can be achieved in multiple-view intervals, such as every 0.3 to 2 msec, to greatly reduce or eliminate any mis-registration between the two kVp data sets, and at the same time provide sufficient data for image reconstruction at the two kVp's.

The term "spectral" used in connection with CT is taken to refer to those techniques to acquire additional information by measuring the subject at more than one different energy since the attenuation of all materials is energy dependent.

The term "gemstone spectral imaging" refers to a type of spectral CT that uses fast kV switching dual energy acquisition technology coupled with a fast sampling, low afterglow, and high light output scintillator detector to produce near perfectly registered dual energy. This data enables projection based material density image generation and the derivation of beam hardening reduced monochromatic spectral images.

Spectral CT techniques are well known to those of skill in the art and are described for example by Lv et al. 2011 Radiology; 259(3): 720-9, Zhang et al. 2011 Med Phys; 38(3): 1178-88 and Delesalle et al. 2013 Radiology; 267(1): 256-66.

In certain embodiments of the invention the method used for spectral CT comprises specific clinically-relevant protocols and settings with non-limiting examples thereof including KVp (Kilovolts peak to peak), mA (milliamps), rotation speed, pitch (rotation speed:table speed) and dose.

In one embodiment of the method of the invention said spectral CT is gemstone spectral imaging (GSI).

In one embodiment of the method of the invention said spectral CT is implemented by alternating kV between multiple energy outputs over the duration of the scan.

In one embodiment of the method of the invention said spectral CT comprises filtration of a primary x-ray beam to create one or more substantially different energy components to the beam.

In one embodiment of the method of the invention said spectral CT is implemented with a dual layer detector that is able to capture high and low energy levels.

In one embodiment of the method of the invention said spectral CT is delivered using energy sensitive detector elements.

In one embodiment of the method of the invention said spectral CT comprises fast and slow switching. In one embodiment of the method of the invention said spectral CT comprises fast switching. In one embodiment of the method of the invention said switching is between 80 kVp and 140 kVp at sub-millisecond speed.

In one embodiment of the method of the invention said spectral CT comprises dual tubes.

In one embodiment of the method of the invention said spectral CT comprises photon counting.

In one embodiment of the method of the invention said spectral CT comprises a dual layer of detectors.

In one embodiment of the method of the invention said spectral CT is dual spectral CT.

In one embodiment of the invention said method differentiates gadolinium retention from retention of one or more other metals. In one embodiment said one or more other metals are selected from zinc, iron and calcium.

In one embodiment of the invention said gadolinium deposition is in the range 0.1-200 μg per gram of tissue.

In one embodiment of the invention said gadolinium deposition is in one or more organs of said subject. In one embodiment said one or more organs is selected from brain, kidney, spleen, liver, skin and bone.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. It will be understood by those of skill in the art that many of the above-described particular embodiments of the invention can be readily combined.

The invention claimed is:

1. A method for antemortem detection and quantification of retained gadolinium deposited in the tissue of a living mammalian subject comprising:
   imaging said living mammalian subject using spectral computed tomography (CT) to obtain an image;
   detecting and quantifying a level of retained gadolinium deposited in the tissue of said living mammalian subject based on an energy-dependent attenuation profile of the retained gadolinium in said living human subject, wherein said level of retained gadolinium deposited in the tissue of said living mammalian subject is in the range 0.1-200 μg per gram of tissue.

2. The method as defined in claim 1 wherein said spectral CT is implemented by alternating kV between multiple energy outputs over the duration of the scan.

3. The method as defined in claim 1 wherein said spectral CT comprises filtration of a primary x-ray beam to create one or more substantially different energy components to the beam.

4. The method as defined in claim 1 wherein said spectral CT is implemented with a dual layer detector that is able to capture high and low energy levels.

5. The method as defined in claim 1 wherein said spectral CT is delivered using energy sensitive detector elements.

6. The method as defined in claim 1 wherein said spectral CT comprises fast and slow switching.

7. The method as defined in claim 6 wherein said spectral CT comprises fast switching.

8. The method as defined in claim 6 wherein said switching is between 80 kVp and 140 kVp at sub-millisecond speed.

9. The method as defined in claim 1 wherein said spectral CT comprises dual tubes.

10. The method as defined in claim 1 wherein said spectral CT comprises photon counting.

11. The method as defined in claim 1 wherein said spectral CT comprises a dual layer of detectors.

12. The method as defined in claim 1 wherein said spectral CT is dual spectral CT.

13. The method as defined in claim 1 wherein said method differentiates gadolinium retention from retention of one or more other metals.

14. The method as defined in claim 13 wherein said one or more other metals are selected from zinc, iron and calcium.

15. The method as defined in claim 1 wherein said tissue comprises one or more organs of said living mammalian subject.

16. The method as defined in claim 15 wherein said one or more organs is selected from brain, kidney, spleen, liver, skin and bone.

* * * * *